United States Patent [19]

Butte, Jr.

[11] 4,070,399
[45] Jan. 24, 1978

[54] HYDROGENATION OF TEREPHTHALNITRILE

[75] Inventor: Walter A. Butte, Jr., West Chester, Pa.

[73] Assignee: Suntech, Inc., Wayne, Pa.

[21] Appl. No.: 724,504

[22] Filed: Sept. 20, 1976

[51] Int. Cl.$^2$ .................. C07C 83/00; C07C 85/00; C07C 87/00; C07C 89/00

[52] U.S. Cl. .................................................. 260/563 D

[58] Field of Search ..................................... 260/563 D

[56] References Cited

U.S. PATENT DOCUMENTS

| | | | |
|---|---|---|---|
| 3,177,258 | 4/1965 | Rylander et al. | 260/563 D X |
| 3,676,495 | 7/1972 | Hoesechele | 260/563 D X |
| 3,742,049 | 6/1973 | Komoto et al. | 260/563 D |

*Primary Examiner*—Paul F. Shaver
*Attorney, Agent, or Firm*—J. Edward Hess; Donald R. Johnson; Paul Lipsitz

[57] ABSTRACT

A process for the preparation of 1,4-bis-(aminomethyl)-cyclohexane by hydrogenating a solvent solution of terephthalonitrile containing at least about 5% by volume of ammonia, said hydrogenation being conducted at a temperature between about 100° and about 150° C, at a pressure of at least about 750 psig, and in the presence of an oxide supported catalyst consisting of from about 10% to 45% by weight of palladium and from about 90% to about 55% by weight of ruthenium.

11 Claims, No Drawings

HYDROGENATION OF TEREPHTHALNITRILE

Aromatic dinitriles such as the phthalonitriles can be hydrogenated to phenylalkylamines with skeletal nickel and cobalt catalysts, but hydrogenation of the aromatic ring does not occur under the conditions ordinarily employed. Further, hydrogenation of the ring structure of phenylalkylamines is difficult presumably because of the known inhibiting effect that strong nitrogen bases exert upon common catalyst systems. Thus, hydrogenation of phenyl alkylamines with Raney nickel requires very severe conditions of temperature and pressure and extensive deamination is encountered (M. Metayer, Bull. Soc. Chim, France, 1952, 276). Platinum catalysts can be used under acidic conditions, but the product is transformed to a salt which must be neutralized in order to isolate the free base (B. L. Zenite, et al. J. Am. Chem. Soc 69, 1117, 1947). U.S. Pat. No. 3,117,162 discloses that rhodium may be used to hydrogenate propionitrile with various solvents, and it was observed that in solvent systems good yield of primary amine could not be obtained. Also, some solvents such as dioxane, chloroform, carbon tetrachloride, etc. poisoned the catalyst. The same patent also discloses use of a rhodium catalyst and a hexane solvent to hydrogenate benzonitrile, but no ring hydrogenation was observed.

U.S. Pat. No. 3,177,258 (Paul N. Rylander, issued Apr. 6, 1965) discloses the hydrogenation of numerous compounds, including aromatic nitriles, using as catalyst a combination of ruthenium with platinum, palladium or rhodium. The catalyst may be supported on carbon, alumina, silica, kieselguhr, $TiO_2$, $CaCO_3$, $BaSO_4$, bentonite and the like. While this patent suggests that the catalyst may be used to hydrogenate nitriles and to reduce aromatic ring structures, there is no indication that such catalysts can be advantageously used for simultaneously hydrogenating both nitrile groups and aromatic rings present in the same molecule.

It has now been found that terephthalonitrile may be efficiently hydrogenated to effect reduction of both the cyano groups and the aromatic ring. Thus, the process of the invention enables terephthalonitrile to be converted to 1,4-bis(aminomethyl)cyclohexane in good yield by a single step hydrogenation technique. In accord with the invention terephthalonitrile is catalytically hydrogenated at a temperature between about 100° C and about 150° C at a pressure of at least about 750 psig, using an oxide supported catalyst consisting of from about 10% to 45% by weight of palladium and from about 90% to about 55% by weight of ruthenium and carrying out the hydrogenation in an inert organic solvent selected from the group of alcohols, ethers and amines, said solvent medium containing at least 5% by volume of ammonia.

As indicated, the process will be carried out in an inert solvent system where the solvent is inert to hydrogenation and such solvents will be selected from the group of alcohols (preferably, lower alkanols), ethers (preferably, cyclic ethers containing five or six atoms in the ring), and amines (most preferably, secondary lower alkyl amines). More specifically, the alkanols preferably employed will be exemplified by methanol, ethanol, isopropanol, n-butanol, hexanol and the like; the ethers may be illustrated by tetrahydrofuran, dioxane, and the like; and the useful amines will include the lower alkyl secondary amines, preferably diethylamine, diisopropylamine, di-n-butylamine, and the like. Also, the reaction product, 1,4-bis(aminomethyl)cyclohexane may also be used as solvent and is also of particular value and a preferred species since it lends itself to a recycle system. Hydrocarbon solvents such as cyclohexane result in poor yields of the desired product.

As indicated, ammonia is also present in the reaction medium and the yield of desired product is quite sensitive to the amount of ammonia used. In order to obtain high yields of the bis-(aminomethyl)cyclohexane, the solvent solution of terephthalonitrile must contain at least about 5% by volume and preferably at least 20% of ammonia. Although there is no critical upper limit for the amount of ammonia, for practical and economic reasons no more than about 30% will be used. Thus, the ratio of ammonia to solvent used will be from about 5:95 to 30:70. The actual amounts of solvent and ammonia are not critical but will be sufficient to dissolve at reaction temperature the desired amount of terephthalonitrile to be treated.

The catalyst composition is also critical for obtaining high yields of product. The catalyst will be a combination of ruthenium and palladium (as metal or oxides) supported on an oxide support. Further, the amount of each metal making up the catalyst is also important for high yields and will contain from about 10% to 45% by weight of palladium, the balance of the catalyst metal being ruthenium. Outside this range the rate of hydrogenation is greatly reduced and there is also a loss of selectivity to the desired product. As indicated, an oxide support is used for the catalyst and may include any of the conventional oxide catalyst supports such as silica, alumina, silica-alumina, boria, titania and the like. The amount of catalyst metal on the support (i.e., Ru plus Pd) will usually be from about 0.5% to about 10% by weight, preferably about 1% to about 5%.

It is possible to use recycled catalyst in the process of the invention, but catalyst which has been used for more than about 15 to 20 hours tends to give somewhat lower yields. Accordingly, fresh catalyst or catalyst recycled only several times is preferred.

Reaction conditions for the process of the invention are quite mild and it is surprising that hydrogenation of the ring occurs under such mild conditions. The temperature of the reaction is also particularly critical to obtain high yields and must be between about 100° C and 150° C, preferably 120° to 140° C. Likewise, the pressure conditions for the reaction are relatively low, being on the order of at least 750 psig, preferably above 1000 psig, but there is no need to exceed about 2500 psig.

In carrying out the process of the invention the terephthalonitrile, solvent, ammonia, and catalyst are charged to the appropriate pressure reactor and, after closing the reactor, it is heated up to about 100° to about 150° C. At this point hydrogen is pressured in to the desired pressure and as stirring or other agitation is maintained the uptake of hydrogen is observed. After hydrogen absorption stops, stirring is continued for a short time, the reactor cooled, opened and the contents filtered. The filtrate is distilled to separate solvent from the product. Isolation and purification of the product is readily accomplished by vacuum distillation.

It will be understood, of course, that in addition to carrying out the process by the batch technique described above, a continuous operation may also be used. In such a case, a bed of catalyst may be used through which the reaction solution and hydrogen are simultaneously passed.

In order to further illustrate the invention the following examples are given. It should be noted that in some of the examples a small, known quantity of hexadecane was included in the solvent. Its sole function is that of an internal analytical standard for chromatographic analysis and determination of yield. This is common practice in laboratory investigations, but it is optional and would not be normally used in practising the invention commercially.

EXAMPLE 1

Terephthalonitrile (40 g.), 400 ml. 1,4-dioxane solvent containing 10 g. hexadecane (analytical standard), 7 g. catalyst (5% of 71:29, ruthenium:palladium of alumina) and 100 ml. liquid ammonia were charged to a stirred autoclave. The reactor was heated to about 125° C with a resulting pressure rise of about 350 psi. Hydrogen was then introduced to a total pressure of 1500 psi and it was noted that the hydrogen was rapidly absorbed. Stirring was continued at 1500 psi and 125° C for 210 min. at which time the absorption of hydrogen had essentially stopped. The reactor was cooled and vented and a sample of the reactor contents was analyzed by gas chromatography. The yield of 1,4-bis(aminomethyl)cyclohexane was 98 wt. % based on the terephthalonitrile charge.

EXAMPLE 2

Terephthalonitrile (100 g.) was hydrogenated in the presence of 14.0 g. catalyst following the procedure set forth in Example 1. Hydrogen absorption was essentially complete at 270 min. The contents of the autoclave was filtered to remove catalyst and was distilled to recover the solvent. The reaction products were further fractionally distilled at reduced pressure and the distillate fractions were analyzed by gas chromatography. The distillate fractions contained 4.0 g. light by-products, principally p-methylbenzylamine and 4-methylcyclohexylmethylamine; 94.3 g. 1,4-bis-(aminomethyl)cyclohexane, b.p. 125° C at 12.7 mm and 5.1 g. of unidentified high boiling residue.

EXAMPLE 3

Terephthalonitrile (100 g.) was hydrogenated in the presence of 18 g. catalyst following the procedure set forth in Example 1 except that 400 ml. diethylamine solvent was used in place of 1,4-dioxane and the ratio of catalytic metal was 33:77, Pd:Ru. Hydrogen absorption was complete in 225 min. The yield of 1,4-bis(aminomethyl)cyclohexane was 98 wt. % based on terephthalonitrile.

EXAMPLE 4

This example compares the effectiveness of catalysts containing other Pd:Ru ratios used in the practice of the present invention with catalysts containing higher and lower Pd:Ru ratios. Each hydrogenation was carried out according to the procedure set forth in Example 3. The reaction mixture was sampled after 240 min. and analyzed for 1,4-bis(aminomethyl)cyclohexane and para-xylylenediamine, a reaction intermediate and known precursor of 1,4-bis(aminomethyl)cyclohexane. Results are shown in Table 1. The selectivity (mole%) is calculated as the sum of the moles of cyclic diamines present including both para-xylylene diamine and 1,4-bis(aminomethylcyclohexane) divided by the moles of terephthalonitirle charged. The yield of 1,4-bisaminomethylcyclohexane is calculated from the weight determined divided by the weight of terephthalonitrile charged. The rate of 1,4-bis-(aminomethyl)cyclohexane formation is calculated by dividing the weight obtained by the weight of catalyst and the reaction time.

TABLE 1

| Pd:Ru Ratio | Selectivity, Mole % of Cyclic Diamines | 1,4-Bis(aminomethyl)-cyclohexane | |
|---|---|---|---|
| | | Rate wt./wt. cat.-hr. | Yield, wt.% |
| 6:94 | 74 | 0.6 | 41 |
| 11:89 | 92 | 1.2 | 90 |
| 22:78 | 96 | 1.4 | 99 |
| 44:56 | 89 | 1.3 | 92 |
| 67:33 | 72 | 0.7 | 49 |

It can be readily seen from the above tabulation that poor rates and poor selectivity result with catalysts containing Pd:Ru ratios outside the range used in the practice of the present invention.

The following two examples illustrate that ruthenium and palladium alone are not useful catalysts for the preparation of 1,4-bis(aminomethyl)cyclohexane under the conditions employed in practicing the present invention:

EXAMPLE 5

The hydrogenation of terephthalonitrile (40 g.) was carried out with the same amount of ruthenium (5% on alumina) catalyst and using the same procedure as Example 1 except that no Pd was present. After 240 min. reaction time, no 1,4-bis(aminomethyl)cyclohexane was present in the reaction mixture according to chromatographic analysis.

EXAMPLE 6

Terephthalonitrile (20 g.), 400 ml. 1,4-dioxane, 20 g. of 5% Pd/Al$_2$O$_3$ catalyst and 100 ml. ammonia were charged to a stirred autoclave. The reactor was heated to 150° C and pressured with hydrogen to 1500 psi. Hydrogen was absorbed over a period of 30 min. and then essentially stopped. An aliquot of reaction solution was removed and analyzed. No 1,4-bis(aminomethyl)-cyclohexane was detected.

The reaction temperature was raised to 175° C whereupon the absorption of hydrogen resumed. After an additional 120 min. at this temperature, the reaction solution was again analyzed. It contained 13.4 g., 67 wt.% yield of paramethylbenzylamine. No 1,4-bis-(aminomethyl)cyclohexane was detected. This result also illustrates the adverse effect of using temperatures above 150° C in conjunction with catalysts containing palladium.

The advantage of the Pd:Ru catalyst can be seen further by comparing the results of the examples above with the following:

EXAMPLE 7

Hydrogenations were carried out following the procedure set forth in Example 1 except that 6 g. of platinum:ruthenium or rhodium:ruthenium (5% on alumina) was used. The results were as follows:

TABLE 2

| Catalyst | 1,4-Bis(aminomethyl)cyclohexane, Yield % |
|---|---|
| Pt:Ru, 17:83 | 0 |
| Rh:Ru, 17:83 | 33 |

EXAMPLE 8

This example illustrates the poor result obtained with a catalyst support other than that of the present invention.

Terephthalonitrile was hydrogenated according to the procedure set forth in Example 3 except that the catalyst support was carbon. Hydrogen was absorbed rapidly for about 15 min. and very slowly thereafter. The reaction was allowed to continue for 180 min. at which time the reaction mixture was analyzed. A 7% yield of 1,4-bis(aminomethyl)cyclohexane was obtained. The principal product was an unidentified by-product of very low volatility.

EXAMPLE 9

This example further illustrates the useful solvents of the present invention.

A series of hydrogenations carried out according to procedures set forth in Examples 1 and 3 but with various other solvent gave the following results:

TABLE 3

| Solvent | Ammonia, Vol.% | Yield, wt.% 1,4-bis(aminomethylcyclohexane |
|---|---|---|
| tetrahydrofuran, $NH_3$ | 20 | 99 |
| ethanol, $NH_3$ | 20 | 100 |
| cyclohexane, $NH_3$ | 20 | 40 |
| diethylamine, $NH_3$ | 10 | 102 |
| diethylamine, $NH_3$ | 5 | 95 |
| diethylamine | — | 78 |

The advantage of at least 5 vol. percent ammonia in combination with an amine, ether or alcohol over a hydrocarbon solvent can be seen from the above tabulation.

EXAMPLE 10

Terephthalonitrile was hydrogenated following the procedure of Example 2 with ethanol as solvent but at a pressure of 500 psi. After 300 min. the reaction product was analyzed. It contained 8% yield of 1,4-bis-(aminomethyl)cyclohexane and much byproduct showing that good results cannot be obtained at a pressure less than 750 psi.

EXAMPLE 11

Terephthalonitrile (130 g.) was hydrogenated with 22 g. catalyst according to the procedure of Example 1 except that the temperature was 90° C. Hydrogen absorption essentially stopped about 60% of theoretical. The temperature was raised to above 100° C whereupon hydrogen absorption resumed illustrating that a temperature greater than about 100° C is necessary to complete the reaction.

EXAMPLE 12

Terephthalonitrile was hydrogenated following the procedure of Example 3 except that the pressure was 2500 psi. Hydrogen absorption was complete after 150 min. The product was filtered free of catalyst and distilled to remove the solvent. Analysis and distillation showed that 1,4-bis(aminomethyl)cyclohexane was the principal product. Minor amounts of 4-methylcyclohexylmethylamine, 3%; 4-methylbenzylamine, 3% and unidentified high boiling amines, 6%, were also formed.

EXAMPLE 13

Terephthalonitrile (160 g.) in 400 ml. of 1,4-dioxane and 100 ml. of ammonia was hydrogenated for 200 minutes at 125°–130° C over 28 g. of catalyst (5% of 29:71, Pd:Ru). The reaction mixture was distilled to remove dioxane leaving a slurry of catalyst in the crude 1,4-bis(aminomethyl)cydohexane. This slurry was recharged together with 64 g. of terephthalonitrile and 50 ml. of ammonia to a 1. stirred autoclave. The mixture was hydgrogenated at 1500 psi. and 125° C for 120 min. A sample was removed and analyzed by gas chromatography. It contained 86% 1,4-bis(aminomethyl)cyclohexane, 10% light byproducts and 4% heavy byproducts. No unreacted terephthalonitrile of aromatic diamine was detected.

The invention claimed is:

1. A process for the preparation of 1,4-bis(aminomethyl)cyclohexane by hydrogenating an inert solvent solution of terephthalonitrile containing at least about 5% by volume of ammonia, said solvent being selected from the group of alcohols, ether and amines, said hydrogenation being conducted at a temperature between about 100° and about 150° C, at a pressure of at least about 750 psig, and in the presence of oxide supported catalyst consisting of from about 10% to 45% by weight of palladium and from about 90% to about 55% by weight of ruthenium.

2. The process of claim 1 wherein the solvent is a lower alkanol.

3. The process of claim 2 wherein the solvent is ethanol.

4. The process of claim 1 wherein the solvent is a cyclic ether having five to six atoms in the ring.

5. The process of claim 4 wherein the solvent is tetrahydrofuran.

6. The process of claim 4 wherein the solvent is dioxane.

7. The process of claim 1 wherein the solvent is an amine.

8. The process of claim 7 wherein the solvent is a secondary lower alkyl amine.

9. The process of claim 8 wherein the solvent is diethylamine.

10. The process of claim 1 where the solvent is 1,4-bis(aminomethyl)cyclohexane.

11. The process of claim 10 wherein a portion of the product is recycled as solvent for the process.

* * * * *